(12) United States Patent
Firoozmand et al.

(10) Patent No.: US 11,529,307 B2
(45) Date of Patent: Dec. 20, 2022

(54) INSOLUBLE AND DISPERSIBLE PROTEIN AND DYE-CONTAINING PARTICLES FOR USE AS COLORANTS

(71) Applicant: Wisconsin Alumni Research Foundation, Madison, WI (US)

(72) Inventors: Hassan Firoozmand, Madison, WI (US); Richard Hartel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 16/762,975

(22) PCT Filed: Nov. 13, 2018

(86) PCT No.: PCT/US2018/060594
§ 371 (c)(1),
(2) Date: May 11, 2020

(87) PCT Pub. No.: WO2019/099338
PCT Pub. Date: May 23, 2019

(65) Prior Publication Data
US 2020/0268645 A1   Aug. 27, 2020

Related U.S. Application Data

(60) Provisional application No. 62/586,252, filed on Nov. 15, 2017.

(51) Int. Cl.
| | | |
|---|---|---|
| *A61K 8/99* | (2017.01) |
| *A23L 5/46* | (2016.01) |
| *A23L 5/44* | (2016.01) |
| *A23L 5/47* | (2016.01) |
| *A61K 8/60* | (2006.01) |
| *A61K 8/64* | (2006.01) |
| *A61K 8/92* | (2006.01) |
| *A61K 47/26* | (2006.01) |
| *A61K 47/44* | (2017.01) |
| *A61K 47/46* | (2006.01) |

(52) U.S. Cl.
CPC .................. *A61K 8/99* (2013.01); *A23L 5/44* (2016.08); *A23L 5/46* (2016.08); *A23L 5/47* (2016.08); *A61K 8/60* (2013.01); *A61K 8/64* (2013.01); *A61K 8/92* (2013.01); *A61K 47/26* (2013.01); *A61K 47/44* (2013.01); *A61K 47/46* (2013.01); *A23V 2002/00* (2013.01)

(58) Field of Classification Search
CPC ... A61K 8/99; A61K 8/60; A61K 8/64; A61K 8/92; A61K 47/26; A61K 47/44; A61K 47/46; A23L 5/44; A23L 5/46; A23L 5/47; A23L 5/43; A23L 5/40; A23V 2002/00; C09B 67/0097
See application file for complete search history.

(56) References Cited

U.S. PATENT DOCUMENTS

2008/0125499 A1* 5/2008 Jensen .................. A61K 9/146
516/69

FOREIGN PATENT DOCUMENTS

JP        S63 188363 A        8/1988

\* cited by examiner

*Primary Examiner* — Robert A Wax
*Assistant Examiner* — Quanglong N Truong
(74) *Attorney, Agent, or Firm* — Boyle Fredrickson S.C.

(57) ABSTRACT

Colorant particles made from an insoluble protein-based substrate to which a dye is adsorbed are disclosed. The colorant particles are highly dispersible onto solid surfaces or within liquid systems, and thus can be used as substitutes for the alumina-based lake particles that are conventionally used as colorants in consumer products, such as food or beverage products, cosmetic products, pharmaceutical products, nutraceutical products, or toys.

17 Claims, 14 Drawing Sheets

INSOLUBLE AND DISPERSIBLE PROTEIN AND DYE-CONTAINING PARTICLES FOR USE AS COLORANTS

CROSS-REFERENCE TO RELATED APPLICATIONS

This application claims the benefit of U.S. provisional Application No. 62/586,252 filed on Nov. 15, 2017, which is incorporated by reference herein in its entirety.

STATEMENT REGARDING FEDERALLY SPONSORED RESEARCH OR DEVELOPMENT

This invention was made with government support under 2014-67017-21652 awarded by the USDA/NIFA. The government has certain rights in the invention.

FIELD OF THE INVENTION

This invention relates generally to dyes that are used to color foods, pharmaceuticals, cosmetics, and other consumer products. In particular, the present invention is directed to protein-based alternatives to the metal salt-based lakes that are conventionally used as colorants in such products.

BACKGROUND OF THE INVENTION

When coloring food and other consumer products, water is the main carrier used to deliver dissolved dye molecules and to stain the food (or other product) matrix. However, water may also transfer the dye out of or within the food matrix, causing color quality deterioration. To overcome these shortfalls, metal salt-based lakes are conventionally used as color pigments and colorants in food materials and in other consumer products.

Lakes are substrates with dye molecules adsorbed to the surface of the substrate. They are insoluble in water but can be dispersed in a medium to modify color and light scattering properties. They can include either organic or inorganic coloring materials (dyes).

Lakes are made by precipitation of a soluble dye onto an insoluble base. Conventionally, insoluble metallic salts such as barium sulfate, calcium sulfate and aluminum hydroxide are used as the base for insoluble lakes. In one example for food and other applications, sodium carbonate is added to a solution of aluminum sulfate, and then a permitted dye is added to the mixture. The dye adsorbs chemically onto surface of the aluminum hydroxide, after which the slurry is washed, dried and ground to a fine powder. The resulting colored powder could be mixed with a carrier or diluent such as vegetable oil, propylene glycol, glycerol, sugar syrup or other media for final application.

Such lakes can be used in a wide variety of consumer product applications. Non-limiting examples include coloring confectionery pieces, such as coloring chocolate or compound coatings (dispersed in oil) or for hard panning (dispersed in sugar) in order to dye the outside of a product such as a gum ball or M&M™ type product. Other exemplary applications include as colorants in pharmaceutical tablets or pills, or use within the matrix to color personal care products such as lipsticks, eye-shadow, nail polishes and lotions.

Despite the widespread applications of alumina-based lakes in foods and other consumer products, there are drawbacks and restrictions in their use. Aluminum, the key element in lakes, has been implicated as a possible contributing factor to dementia, specifically Alzheimer disease (Yokel, R. A., *Aluminum in food—the nature and contribution of food additives*, in Food Additive, Y. El-Samragy, Editor 2012, Intech: Rijeka, Croatia. p. 203-228). Tolerable intake and minimal risk levels of Aluminum in foods are under consideration, leading to restrictions in its use in food and other consumer products. For example, in confection products in general, the use of alumina-based lakes is restricted to a maximum concentration of 70 ppm (McAvoy, S. A., *Global Regulations of Food Colors*. The Manufacturing Confectioner, 2014. 94(9): p. 77-86).

Accordingly, there is a need in the art for alternatives to alumina-based lakes that can be safely and effectively used as colorants in foods and other consumer products.

SUMMARY

To overcome the limitations of conventional metal salt-based lakes, we have developed alternative lakes having an insoluble, dispersible protein-containing substrate instead of an insoluble metal salt-based substrate, such as alumina. Dyes are adsorbed onto the protein-containing substrate, resulting in a dye and protein-containing particle that can act as a colorant pigment for various applications, such as in food, pharmaceutical, or cosmetic products. Because the protein substrates include substances that have been a part of human diet for centuries and/or are widely used in the food industry, they can safely be used in food and other consumer products.

In a first aspect, the disclosure encompasses a colorant particle that includes (a) an insoluble substrate that includes one or more proteins; and (b) a dye that is adsorbed onto the insoluble substrate. The colorant particle is both insoluble in a liquid system and dispersible within a liquid system or onto a solid surface.

In some embodiments, the liquid system is aqueous or includes a non-polar solvent. In some such embodiments, the non-polar solvent is a fat.

In some embodiments, the solid surface includes or consists essentially of a sugar.

In some embodiments, the insoluble substrate is not (a) part of or all of a tissue sample from a multicellular organism; or (b) part of or all of a living single-celled organism.

In some embodiments, the insoluble substrate is less than 10%, less than 5%, or less than 1% insoluble metal salts by weight. In some such embodiments, the insoluble substrate is substantially free of insoluble metal salts.

In some embodiments, the insoluble substrate is less than 10%, less than 5%, or less than 1% alumina by weight. In some such embodiments, the insoluble substrate is substantially free of alumina.

In some embodiments, the insoluble substrate is part of or all of a biologically inactivated single-celled microorganism. In some such embodiments, the biologically inactivated single-celled microorganism is a bacterium or a yeast. In some such embodiments, the biologically inactivated single-celled microorganism is an edible biologically inactivated single-celled microorganism. In some such embodiments, the edible biologically inactivated single-celled microorganism is a lactic acid bacterium, a baker's yeast, or a brewer's yeast. In some such embodiments, the edible biologically inactivated single-celled microorganism is of the genus *Lactobacillus*, *Lactococcus*, or *Saccharomyces*.

In some embodiments, the insoluble substrate includes a microparticulated protein. In some such embodiments, the microparticulated protein is a microparticulated whey protein or a textured plant protein.

In some embodiments, the length of the insoluble substrate, as measured across the longest axis, the shortest axis, or any intermediate axis, is from about 0.10 micrometers to about 10.0 micrometers.

In some embodiments, the colorant particle is highly dispersible within the liquid system or onto the solid surface, such that when dispersed, the dispersion density of the colorant particles within any two portions of the liquid system or the solid surface does not vary by more than 20%.

In some embodiments, the adsorbed dye is a synthetic dye or a naturally-occurring dye.

In a second aspect, the disclosure encompasses a composition that includes two or more colorant particles as described above, where the colorant particles are dispersed within a liquid system, within a solid, or onto a solid surface.

In some embodiments, the liquid system is aqueous or includes a non-polar solvent. In some such embodiments, the non-polar solvent is a fat.

In some embodiments, the solid surface includes or consists essentially of a sugar.

In some embodiments, the colorant particles are highly dispersed within the liquid system, within the solid, or onto the solid surface, such that the dispersion density of the colorant particles within any two portions of the liquid system, solid, or solid surface does not vary by more than 20%.

In some embodiments, the composition has a different color than the composition would have in the absence of the two or more colorant particles. In some such embodiments, the color difference is detectable with the naked eye.

In some embodiments, the composition is part of or all of a consumer product. In some such embodiments, the consumer product is a food or beverage product, a cosmetic product, a pharmaceutical product, a nutraceutical product, or a toy.

In a third aspect, the disclosure encompasses a consumer product that includes the colorant particle as described above.

In some embodiments, two or more of the colorant particles are dispersed within a liquid system, within a solid, or onto a solid surface.

In some embodiments, the consumer product is a food or beverage product, a cosmetic product, a pharmaceutical product, a nutraceutical product, or a toy.

In a fourth aspect, the disclosure encompasses the use of the colorant particle as described above to impart color to part or all of a consumer product.

In some embodiments, the consumer product is a food or beverage product, a cosmetic product, a pharmaceutical product, or a nutraceutical product.

In a fifth aspect, the disclosure encompasses a method for coloring a consumer product. The method includes the step of contacting a precursor system that ultimately forms part or all of the consumer product with two or more colorant particles as described above. As a result of performing the method, the two or more colorant particles become dispersed within or on the precursor system.

In some embodiments, the precursor system is a liquid system or a solid surface. In some such embodiments, the liquid precursor system is aqueous or includes a non-polar solvent. In some such embodiments, the colorant particles become highly dispersed within the liquid precursor system or onto the solid surface, such that the dispersion density of the colorant particles within any two portions of the liquid precursor system or solid surface does not vary by more than 20%.

In some embodiments where the precursor system is a liquid system, the method further includes the step of gelling, thickening or solidifying the liquid precursor system.

In some embodiments, the method further includes incorporating the precursor system into the consumer product.

In some embodiments, the consumer product is a food or beverage product, a cosmetic product, a pharmaceutical product, a nutraceutical product, or a toy.

In a sixth aspect, the disclosure encompasses a method of making a colorant particle. The method includes the step of adsorbing a dye onto an insoluble substrate that includes one or more proteins. As a result of performing the method, a colorant particle that is both insoluble in a liquid system and dispersible within the liquid system or onto a solid surface is produced.

In some embodiments, the insoluble substrate is not (a) part of or all of a tissue sample from a multicellular organism; or (b) part of or all of a living single-celled organism.

In some embodiments, the insoluble substrate is substantially free of alumina.

In some embodiments, the insoluble substrate is part of or all of a biologically inactivated single-celled microorganism. In some such embodiments, the biologically inactivated single-celled microorganism is an edible single-celled microorganism. In some such embodiments, the edible biologically inactivated single-celled microorganism is a lactic acid bacterium, a baker's yeast, or a brewer's yeast. In some such embodiments, the edible biologically inactivated single-celled microorganism is of the genus *Lactobacillus*, *Lactococcus*, or *Saccharomyces*.

In some embodiments, the insoluble substrate includes a microparticulated protein. In some such embodiments, the microparticulated protein is microparticulated whey protein or microparticulated textured plant protein.

In some embodiments, the adsorbed dye is a synthetic dye or a naturally-occurring dye.

In some embodiments, the method further includes the step of dispersing two or more of the resulting colorant particles within a liquid system or onto a solid surface.

In a seventh aspect, the disclosure encompasses a method of making a colorant particle from a biologically inactivated single-celled microorganism or a microparticulated protein particle. The method includes the steps of (a) adding a dye to and acidifying an aqueous solution that is in contact with a biologically inactivated single-celled microorganisms or microparticulated protein particle; and (b) subsequently raising the pH of the aqueous solution that is in contact with the biologically inactivated single-celled microorganism or microparticulated protein particle. As a result of performing the method, the dye is stably adsorbed to the biologically inactivated single-celled microorganism or microparticulated protein particle to form a colorant particle.

In some embodiments, step (a) of acidifying the aqueous solution includes lowering the pH of the aqueous solution to below 4.0. In some such embodiments, the pH of the aqueous solution is lowered to 2.0 or below. In some such embodiments, the pH of the aqueous solution is lowered to between 1.0 and 2.0.

In some embodiments, step (b) of subsequently raising the pH of the aqueous solution includes raising the pH of the aqueous solution to above 6.0. In some such embodiments, the pH of the aqueous solution is raised to above 6.8. In some such embodiments, the pH of the aqueous solution is raised to between 6.8 and 7.6.

In some embodiments, the method further includes the step of drying the resulting colorant particle. In some such embodiments, the temperature of drying is changed, in order to modify the color of the colorant particle.

In some embodiments, the method further includes the step of changing the temperature of the aqueous solution, in order to modify the color of the colorant particle and/or binding stability of the dye.

These and other features will become apparent to the skilled artisan from the following detailed description considered in conjunction with the accompanying drawings.

DETAILED DESCRIPTION OF THE INVENTION

I. In General

Figure 1:
FIG. 1 is a black and white version of a color photograph showing inactive dried lactic bacteria colored with spirulina dye (blue), chlorophyll dye (green), carmine dye (red), and turmeric dye (yellow). The black and white version of the photograph does not show the colors, but each lactic acid bacteria sample is labeled below with the color that appears in the original color photograph.

The disclosed invention is not limited to the particular methodology, protocols, materials, and reagents described, as these may vary. Furthermore, the terminology used herein is for the purpose of describing particular embodiments only, and is not intended to limit the scope of the present invention, which will be defined only by the claims of any later-filed nonprovisional applications.

As used herein and in the appended claims, the singular forms "a", "an", and "the" include plural reference unless the context clearly dictates otherwise. Furthermore the terms "a" (or "an"), "one or more" and "at least one" can be used interchangeably, and the terms "comprising", "including", and "having" can be used interchangeably.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the disclosed invention, non-limiting methods and materials are now described. All publications and patents specifically mentioned herein are incorporated by reference for all purposes, including for describing and disclosing the chemicals, instruments, statistical analysis and methodologies that are reported in the publications. All references cited in this specification are to be taken as indicative of the level of skill in the art.

As used herein, the term "about" means within a range from 10% below to 10% above a given value.

II. The Invention

The inventors have developed protein-based colorant particles that can be substituted for the insoluble metal salt-based lake pigments, such as alumina-based lakes, that are commonly used as colorants in foods, pharmaceuticals, cosmetics, toys, and other consumer products. The colorant particles are made up of an insoluble protein-containing substrate to which one or more dyes are adsorbed. Like conventional lakes, the disclosed protein-based colorant particles are both insoluble in and highly dispersible within one more liquid systems (or onto one or more solid surfaces) that form part of or all of a consumer product or a precursor of a consumer product. Accordingly, the protein-containing substrate must itself be insoluble in one or more liquid systems, while at the same being capable of uniform dispersion within such systems. The nature of the protein-containing substrate and the dye is not otherwise limited, although certain exemplary embodiments are described in more detail below.

A. Protein-Containing Substrate

As noted above, the protein-containing substrate must be insoluble but dispersible within one or more liquid systems. Such liquid systems may include aqueous solutions or liquid systems that include a non-polar solvent, such as fat-based systems.

In some embodiments, the protein-containing substrate is capable of being highly dispersed in one or more liquid systems. In some such embodiments, when dispersed within one or more liquid systems, the protein-containing substrate exhibits a dispersion density variation within the liquid system that is less than 50%, less than 45%, less than 40%, less than 35%, less than 30%, less than 25%, less than 20%, less than 15%, less than 14%, less than 13%, less than 12%, less than 11% or less than 10%.

The protein-containing substrate may in some embodiments also include other substances, such as polysaccharides, peptidoglycans, and/or nucleic acids. In some embodiments, the protein-containing substrate may be part or all of a deactivated single-celled microorganism. In some such embodiments, the single-cells microorganism is "edible," meaning that it is a species of microorganism that commonly consumed as an ingredient in foods or beverages. Non-limiting examples of edible microorganisms include lactic acid bacteria (e.g., *lactobacillus* or *lactococcus*) and baker's and brewer's yeast (*Saccharomyces cerevisiae*). In some embodiments, the protein-containing substrate may be formed by aggregating and/or denaturing a protein to make it insoluble. In some embodiments, the protein-containing substrate may be a microparticulated protein product. Non-limiting examples include microparticulated whey protein (e.g., SIMPLESSE®) and microparticulated textured plant protein (e.g., textured vegetable protein, TVP or textured soy protein, TSP).

In some embodiments, the protein-containing substrate is not part or all of a tissue sample from a multicellular organism, nor is it part or all of a living single-celled organism.

In some embodiments, the protein-containing substrate does not include one or more substances that would be present in conventional lake pigments, or the protein-containing substrate includes such substances in concentrations far below the concentrations of such substances in conventional lake substrates. For example, in some embodiments, the protein-containing substrate contains less than 20%, less than 18%, less than 16%, less than 14%, less than 12%, less than 10%, less than 9%, less than 8%, less than 7%, less than 6%, less than 5%, less than 4%, less than 3%, less than 2%, or less than 1% by weight of an insoluble metal salt, such as alumina. In some such embodiments, the protein-containing substrate is substantially free of an insoluble metal salt, such as alumina.

The size of the protein-containing substrate may affect both its solubility in liquid systems and its ability to be uniformly dispersed within such systems. Accordingly, in some embodiments, the length of one or more of the shortest axis, the longest axis, or an intermediate axis of the protein-containing substrate is within the range from about 0.01 micrometers (microns, μm) to about 15.0 μm. In certain embodiments, the lower limit of this range may be about 0.01 μm, about 0.02 μm, about 0.03 μm, about 0.04 μm, about 0.05 μm, about 0.06 μm, about 0.07 μm, about 0.08 μm, about 0.09 μm, about 0.10 μm, about 0.12 μm, about 0.14 μm, about 0.16 μm, about 0.18 μm, about 0.20 μm, about 0.22 μm, about 0.24 μm, about 0.26 μm, about 0.28 μm, about 0.30 μm, about 0.32 μm, about 0.34 μm, about 0.36 μm, about 0.38 μm, about 0.40 μm, about 0.42 μm, about 0.44 μm, about 0.46 μm, about 0.48 μm, about 0.50 μm, about 0.52 μm, about 0.54 μm, about 0.56 μm, about 0.58 μm, about 0.60 μm, about 0.62 μm, about 0.64 μm, about 0.66 μm, about 0.68 μm, about 0.70 μm, about 0.72 μm, about 0.74 μm, about 0.76 μm, about 0.78 μm, about 0.80 μm, about 0.82 μm, about 0.84 μm, about 0.86 μm, about 0.88 μm, about 0.90 μm, about 0.92 μm, about 0.94 μm, about 0.96 μm, about 0.98 μm, or about 1.0 μm. In certain embodiments, the upper limit of this range may be about 15.0 μm, about 14.0 μm, about 13.0 μm, about 12.0 μm, about 11.0 μm, about 10.0 μm, about 9.5 μm, about 9.0 μm, about 8.5 μm, about 8.0 μm, about 7.5 μm, about 7.0 μm, about 6.5 μm, about 6.0 μm, about 5.5 μm, about 5.0 μm, about 4.8 μm, about 4.6 μm, about 4.4 μm, about 4.2 μm, about 4.0 μm, about 3.8 μm, about 3.6 μm, about 3.4 μm, about 3.2 μm, about 3.0 μm, about 2.9 μm, about 2.8 μm, about 2.7 μm, about 2.6 μm, about 2.5 μm, about 2.4 μm, about 2.3 μm, about 2.2 μm, about 2.1 μm, or about 2.0 μm.

In some embodiments, the protein-containing substrate is considered safe for human contact and/or ingestion. Such embodiments would include all protein-containing substances and compositions (including, without limitation, processed protein products or microorganisms), that are (a) commonly consumed as ingredients in foods or beverages; (b) "food additives" approved by the FDA for human consumption; and/or (c) generally recognized as safe (GRAS). A composition or substance is considered GRAS if its general recognition of safety is based on the views of experts qualified to evaluate the safety of the substance or composition. GRAS status may be based either on a history of safe use in food prior to 1958 or on scientific procedures, which require the same quantity and quality of evidence as would be required to obtain a food additive regulation. Because GRAS status may be either affirmed by the FDA or determined independently by qualified experts, the FDA's regulations do not provide a comprehensive list all GRAS ingredients. See Federal Food, Drug and Cosmetic Act, §§ 201(s) and 409; 21 C.F.R. 170.3 and 21 C.F.R. 170.30.

B. Dye Adsorbed to the Substrate

The precise chemical nature and source of any the dye used, whether it is obtained organically or synthetically, is not limited. The dye examples presented below (chlorophyll, spirulina dye, carmine dye, turmeric dye, annatto dye, anthocyanin dye, beta-carotene dye) are intended merely as illustrative, and cannot be construed as limiting the specific dyes that can be utilized.

In some embodiments the dye may be considered safe for human contact and/or ingestion, as discussed above.

C. Use of the Colorant Particles in Consumer Products

The disclosed colorant particles can be used to impart a desired color to a wide range of consumer products, including, without limitation, foods and beverages, pharmaceutical products, nutraceutical products, cosmetic products, and toys. In some embodiments, the disclosed colorant particles can be used in any coloring application for which conventional lakes are currently used, without the concerns and limitations associated with aluminum-containing substrates.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

In these non-limiting examples, we provide proof of concept for replacing alumina in lakes with an insoluble protein-based substrate. Specifically, the examples demonstrate the use of inactivated lactic bacteria, inactivated baker's yeast, and microparticulated whey protein, SIMPLESSE®, as the insoluble protein-based substrate. Dyes can be adsorbed to these substrates, and the resulting colorant particle can act as a colorant pigment for various applications, such as in the food, pharmaceutical, and cosmetic industries. Lactic acid bacteria and yeast have been a part of human diet for centuries and microparticulated whey protein, has nutritional and functional applications in food industry. Accordingly, these exemplary substrates as generally recognized as safe for human consumption. Furthermore, these exemplary substrates are insoluble in water and have the proper size and diameter to be effective dye substrates.

Dyes can bind to different components of microbial cells based on their charge affinity; positively charged dyes bind with negatively charged cellular components such as nucleic acids (DNA and RNA) and acidic polysaccharides. Negatively charged dyes bind with positively charged cellular components, such as proteins. The ability of lactic bacteria to adsorb dyes is related to their cell surface properties, governed by surface-bound proteins, polypeptides and polysaccharides. Lactic bacteria have a thick peptidoglycan layer in their cell wall that retains the dye and prevents the dye from leaching out. Ability of lactic bacteria to retain dye and provide coloring effect is possibly due to the restriction of dye migration through the peptidoglycan-teichoic acid within the bacteria cell wall (Sträuber, H. and S. Müller, Viability states of bacteria—Specific mechanisms of selected probes. *Cytometry Part A*, 2010. 77A(7): p. 623-634). The structure of peptidoglycan in lactic bacteria cell wall is constructed of multilayer long chains of glycan that are crosslinked with flexible peptide bridges together. Dye uptake also is known to be dependent on cell size and surface of microorganisms (Natarajan, A. and F. Srienc, Dynamics of Glucose Uptake by Single *Escherichia coli* Cells. *Metabolic Engineering*, 1999. 1(4): p. 320-333). Similarly, for yeast cells, densely-packed fibrous polysaccharides and mannoproteins on yeast cell walls are assumed to retain dye molecules.

In general, dyes are known to combine with protein groups of opposite ionic charge (Fraenkel-Conrat, H. and M. Cooper, The use of dyes for the determination of acid and basic groups in proteins. *Journal of Biological Chemistry*, 1944. 154: p. 239-246), which provides an opportunity to fix the dye molecules on protein substrates and later insolubilize the proteins in form of aggregates or microparticulated form such as colloidal particles. To this end, commercially available Microparticulated Whey Protein, SIMPLESSE® can also be used as dye binder and dye vehicle to produce dye pigments to carry the functionally of traditional lakes. Each of these exemplary embodiments (inactivated lactic bacteria, inactivated yeast, and microparticulated whet protein) is demonstrated in these examples. However, the scope of the disclosure is not in any way limited by these examples.

Example 1

Preparation of Lactic Bacteria and Yeast Cells

In this example, we describe the procedure used to prepare the lactic bacteria and yeast cells that were used in subsequent examples as insoluble protein-containing substrates used to make substrate-dye colorants. In the examples below, the microparticulated whey protein was used as an exemplary substrate without any prior modification.

Preparation of Lactic Bacteria and Yeast Cells.

Lactic bacteria in the form of frozen pellets packaged in plastic pouch were thawed at room temperature. Afterwards, the pouch content was discharged into a 1 liter beaker and suspended with water at room temperature.

Dry yeast (active or nutritional) were suspended in tap water at 40-10 wt % in a beaker and stirred frequently to uniformly disperse the cells About 30 gram of cell-water (lactic bacteria or Baker's yeast) suspension was transferred to 80 ml centrifuge tube and washed 5-7 times with about 50 gram of water by repeated re-suspension/centrifugation cycles (5 min, 6000 rpm). After each stage of centrifugation, cells sedimented in the bottom of the centrifuge tubes and covered by mucous-like material. Water and the mucous-like material on top of the cell sediment were discarded and cells re-suspended with fresh water. Repeated re-suspension/centrifugation cycles were continued until a clear supernatant (water) and homogeneous cells sediment free of mucous-like material were obtained.

Example 2

Adsorbing Dye to Lactic Bacteria, to Yeast, and to Microparticulated Whey Protein In this example, we describe the main procedure used to stain the cells and microparticulated whey protein particles with a dye and the procedure to set the dye in cells and microparticulated whey protein particles, to form exemplary colorant particles.

In general, dye in the form of liquid or dry powder was directly added to the substrate aqueous suspension. After mixing the dye with substrate suspension, for each specific dye, different times/temperatures/acids/salts were used. Then the suspension was transferred to 80 ml centrifuge tube and washed several times with tap water, alchohol, acid salt solution depending on the dye, by repeated re-suspension/centrifugation washing cycles (5 min, 6000 rpm). After each centrifugation step, supernatant (water and dissolved dye) was discarded and colored sediment was re-dispersed with tap water. Re-suspension/centrifugation cycles were continued until no visible trace of dye was observed in centrifuge tube supernatant (water) and the pH reached the range of 6.8-7. Then the sediment in the centrifuge tube (colored substrate) was discharged and dried at room temperature. The yeast cell lactic bacteria were colored with seven different exemplary dyes: spirulina dye (blue), chlorophyll dye (green), carmine dye (red), turmeric dye (yellow) annatto dye (yellow), beta-carotene dye (orange), and anthocyanin dye (purple). The microparticulated whey protein (SIMPLESSE®) was colored with four different exemplary dyes: spirulina dye (blue), chlorophyll dye (green), carmine dye (red), and turmeric dye (yellow).

Staining the Baker's Yeast and Lactic Bacteria Cells.

Dye in the form of liquid or dry powder was directly added to the aqueous suspension of baker's yeast and lactic bacteria cells and mixed for about 10 minutes. Depending on the dye, to set the dye and prevent dye discharge (dye bleeding), different procedures were employed.

For spirulina dye (blue) by addition of hydrochloric acid solution (3 Normal), the pH of the mixture was lowered to the range of pH 1-2 and mixed for about 5 minutes the stained cell suspension. The mixture was then subjected to elevated temperature by heating to 85-90° C. for 10-15 minutes. Afterward, the mixture was subjected to repeated re-suspension/centrifugation cycles, and a solution of 50 wt % Magnesium Chloride (Mg $Cl_2$) was used 2-3 times while washing the cells in the pH range of 5-6. Washing with tap water was continued until the suspension reached pH 6.5-7.

To set the chlorophyll dye (green), the pH of the mixture was lowered to the range of pH 1-2 by addition of hydrochloric acid solution (3 Normal) and the baker's yeast or lactic bacteria cells suspension mixed for about 5 minutes. The mixture was either subjected to elevated temperature by heating to 85-90° C. for 10-15 minutes, or without heat treatment, the approximate same volume of the ethanol (Ethyl Alcohol) 190 Proof was added to cell suspension. Afterward the mixture was subjected to repeated re-suspension/centrifugation cycles with tap water until the suspension reached pH 6.5-7

To set the carmine dye (red), 2 different procedures were employed. For yeast cells, no heat treatment was used— equal weight of aqueous stained cells suspension (one part)

was added to equal weight of ethanol (Ethyl Alcohol) 190 Proof (one part) and mixed for about 5-10 minutes. Then equal weight of tannic acid solution 40 wt % (one part) was added to alcoholic stained cell suspension. The mixture (3 parts) was kept at 40° C. and mixed for about 16 hours. Afterward, the mixture was subjected to repeated re-suspension/centrifugation washing cycles and for 2-3 times the mixture was washed with tannic acid solution ≤40 wt % and again with tap water until the suspension reached pH 6.5-7. For Bacteria, similar procedure to yeast treatment was used, but with longer time/temperature treatment, such as over 24 hours at 40° C. Afterward, the mixture was subjected to repeated re-suspension/centrifugation washing cycles with tap water until the suspension reached pH 6.5-7.

To set turmeric dye (yellow), the pH of the stained cell suspension was lowered by addition of hydrochloric acid solution (3 Normal) to the range of pH 1-2, but no heat treatment was used. The mixture was washed by re-suspension/centrifugation cycles until pH reached the range of 6.8-7.

To set the annatto dye (yellow), 2 different procedures for yeast and lactic bacteria were used. For yeast cell, by addition of hydrochloric acid solution (3 Normal), the pH of the mixture was lowered to the range of pH 1-2 and was mixed for about 5 minutes the stained baker's yeast cells. The mixture was then subjected to elevated temperature by heating to 85-90° C. for 10-15 minutes. Afterward, the mixture was subjected to repeated re-suspension/centrifugation cycles. At the pH range of 5-6, ethanol (Ethyl Alcohol) 190 Proof was used 2-3 times while washing the cells and washing with tap water was continued to until the suspension reached to pH 6.5-7. For lactic bacteria, no heat treatment was used. Equal weight of aqueous stained cells (one part) was mixed with equal weight (one part) of solution of 50 wt % Magnesium Chloride (Mg $Cl_2$) and with equal weight (one part) ethanol (Ethyl Alcohol) 190 Proof and with equal weight (one part) of hydrochloric acid solution (3 Normal). Then the mixture (4 parts) was mixed for 10-15 min. Afterwards, the mixture was subjected to repeated re-suspension/centrifugation cycle until the suspension reached to pH 6.5-7.

To set beta-carotene dye (orange), 2 different procedures for yeast and lactic bacteria were used. For yeast cells, the pH of the mixture was lowered by addition of glacial acetic acid to the range of pH 1-2 and mixed for about 5 minutes the stained baker's yeast cells suspension. The mixture was subjected to elevated temperature by heating to 85-90° C. for 5 minutes. The mixture was subjected to repeated re-suspension/centrifugation cycles and ethanol (Ethyl Alcohol) 190 Proof was used 2-3 times while washing the cells suspension in the pH range of 5-6. Washing with tap water was continued until the suspension reached pH 6.5-7. For lactic bacteria, no heat treatment was used. Aqueous stained cells suspension (one part) was mixed with equal weight (one part) of ethanol (Ethyl Alcohol) 190 Proof and equal weight (one part) glacial acetic acid. Then the mixture (3 parts) was mixed for 10-15 min. Afterwards, the mixture was subjected to repeated re-suspension/centrifugation whashing cycle with tap water until the suspension reached pH 6.5-7.

To set the anthocyanin dye (purple), 2 different procedures for yeast and lactic bacteria were used. For yeast cells, the pH of the stained cell suspension was lowered by addition of glacial acetic acid to the range of pH 1-2 and mixed for about 5 minutes the stained baker's yeast cells suspension. The mixture was subjected to elevated temperature by heating to 85-90° C. for 5 minutes. The mixture was subjected to repeated re-suspension/centrifugation washing cycles and ethanol (Ethyl Alcohol) 190 Proof was used 2-3 times while washing the cells suspension in the pH range of 5-6. Washing with tap water was continued until the suspension reached pH 6.5-7. For lactic bacteria, no heat treatment was used. Aqueous stained cells suspension (one part) was mixed with equal weight (one part) of solution of 50 wt % Magnesium Chloride (Mg $Cl_2$) and with equal weight (one part) of ethanol (Ethyl Alcohol) 190 Proof and with equal weight (one part) glacial acetic acid. Then the mixture (4 part) was mixed for 10-15 min. Afterwards, the mixture was subjected to repeated re-suspension/centrifugation washing cycle until the suspension reached the range of pH 6.5-7.

Staining the Microparticulated Whey Protein.

Dye in the form of liquid or dry powder was directly added to the aqueous suspension of Microparticulated whey protein. The pH of the mixture was lowered to the range of pH 1-2 by addition of glacial acetic acid and mixing continued for around 5 to 10 minutes. The mixture was subjected to elevated temperature, up to 95° C. for 3-5 minutes, and afterward the mixture subjected to repeated re-suspension/centrifugation washing cycle until the suspension reached pH 6.5-7.

Elevated temperature, up to 95° C. for 3-5 minutes, can be used to fortify the dye binding to substrate in aqueous suspension of cells or microparticulated whey protein on acidic condition; however, the intensity of the dye reduces and these conditions may decompose the dye molecules. Nonetheless, the elevated temperature can be used to generate different shades of color on the substrate (cells and microparticulated whey protein). Extrusion process, high pressure and heat can be used to bind the dye molecules to protein substrate.

In an industrial setting, it is possible to add (those) natural dyes to a fermentation tank, where the baker's yeast and lactic bacteria propagate. Natural dyes can be adsorbed by the cell wall during cell growth as the pH of the growth medium decreases due to cell metabolism. Modification of the growth broth and encouraging the living cells to up take certain ions may also enhance the dye intake by cells. For example, existing $Ca^{+2}$ in cells may facilitate precipitation and up-take of norbixin, (the solubilized bixin), the major pigment of annatto dye by the cells.

Temperature of pigment drying also affects the color of the dyed substrate. The higher drying temperature causes darker tone in the color of the resulted pigments. The color of the dyed substrates remains vivid and brighter at lower drying temperature or ambient drying.

Figure 2:
FIG. 2 is black and white version of a color photograph showing inactive dried baker's yeast colored with spirulina dye (blue), chlorophyll dye (green), carmine dye (red), annatto dye (yellow). The black and white version of the photograph does not show the colors, but each lactic acid bacteria sample is labeled below with the color that appears in the original color photograph.

FIG. 1 and FIG. 2 show the colored and dried lactic bacteria (FIG. 1) and baker's yeast cells (FIG. 2) with natural 4 main colors, such as blue (spirulina), green (chlorophyll), red (carmine), yellow (turmeric and annatto).

Example 3

Dye Retention Test Results

Retention of the dyes adsorbed onto deactivated lactic bacteria, deactivated yeast, or microparticulated whey protein substrates demonstrates that colored deactivated microbial cells and protein particles can be used as substrates to form all natural, safe-to-eat color pigments. Colored cells and colored microparticulated whey protein could replace aluminate lakes in various industries, including, without limitation, the food, pharmaceutical, and cosmetic industries. The colorants could also be used in other chemical industry applications. For example, crayons for toddlers could be manufactured using such colorants. The dried colored lactic bacteria, yeast cells and microparticulated proteins could be dispersed into the product or be coated on the surface of the product, based on the specific application.

Desorption or dissolution of the dye from the lake dye into a solution is referred to as "bleeding". To test the bleeding characteristic of colored cells, the test procedure used in industry is employed. That is, an aqueous suspension of 5 wt % colored cells was prepared by dispersing the required dried colored cells in water. The suspensions were mixed with magnetic stirrer for 10 minutes. Aliquots of cell suspension were filtered through a 0.45 μm PTFE membrane filter through disposable syringe filter (mdi, SY13TF), and the filtrate was assayed for dye. The amount of the dye dissolved from the colored cells was monitored using visible spectrophotometry.

Figure 3A:
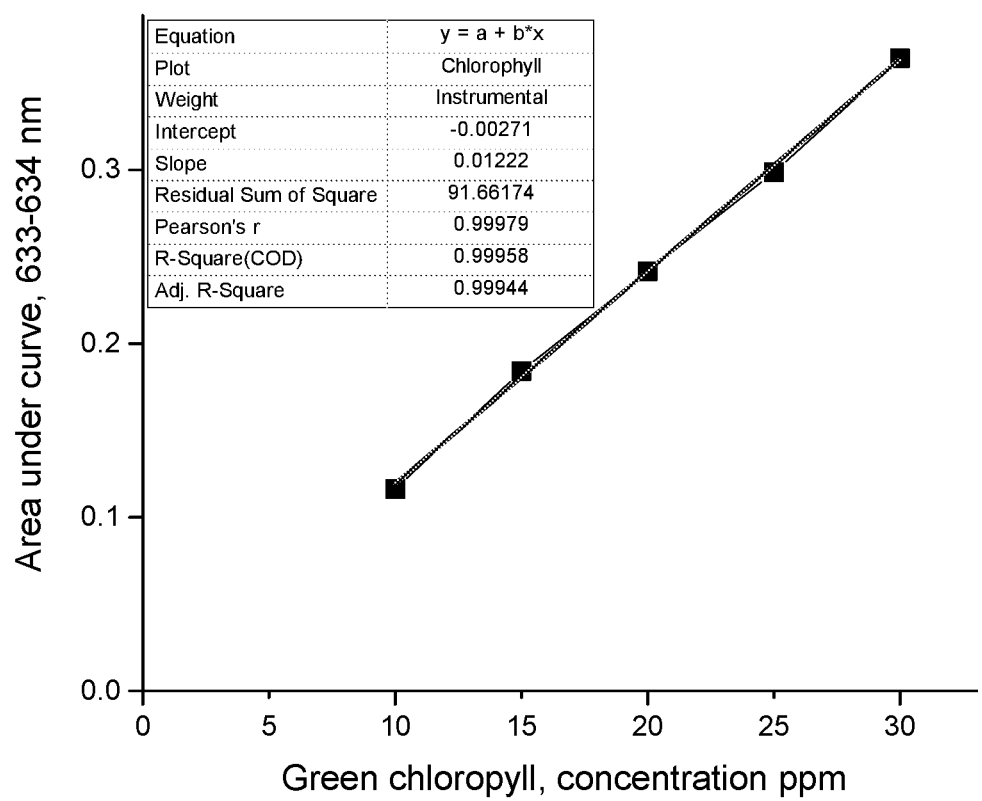
FIG. 3A shows a Beer's law standard concentration curve for green chlorophyll.
Figure 3B:
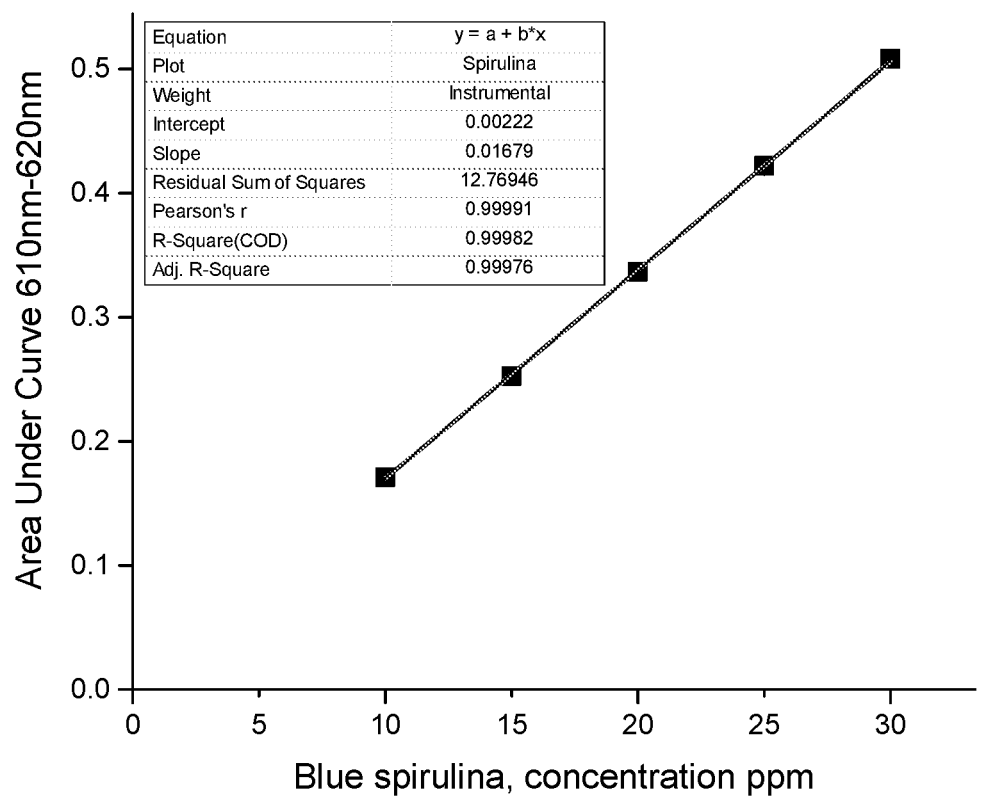
FIG. 3B shows a Beer's law standard concentration curve for blue spirolina.
Figure 3C:
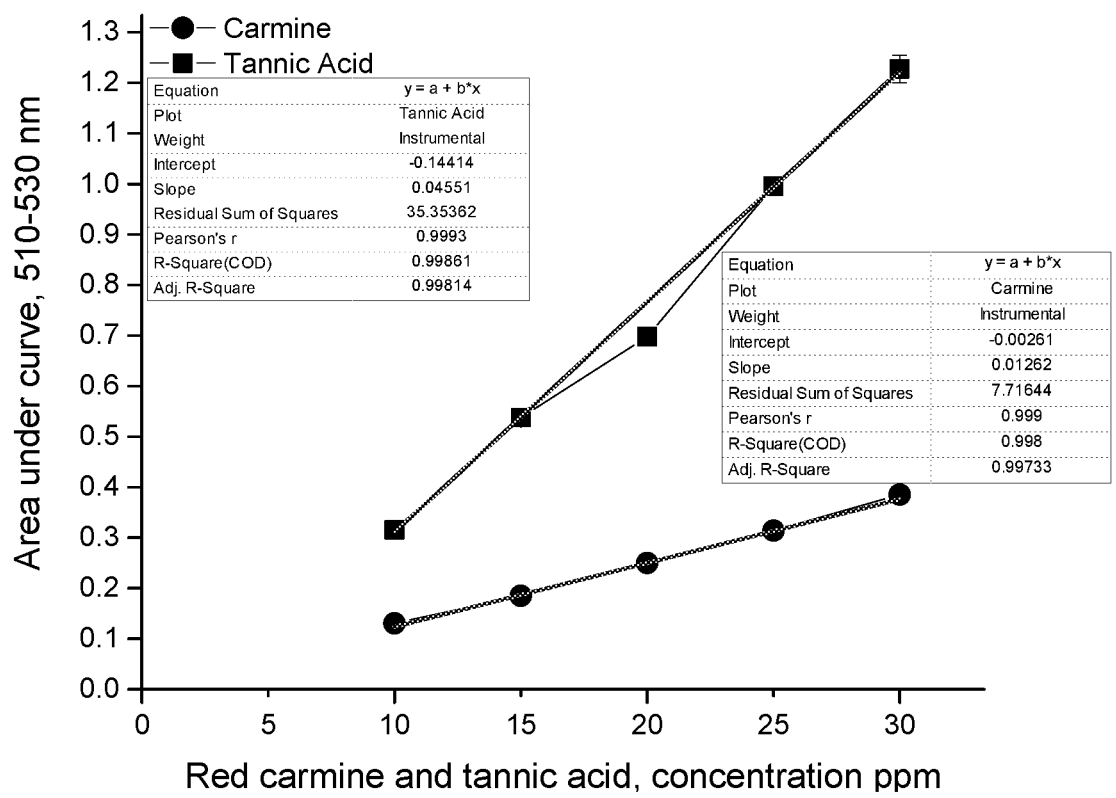
FIG. 3C shows Beer's law standard concentration curves for red carmine and tannic acid.
Figure 3D:
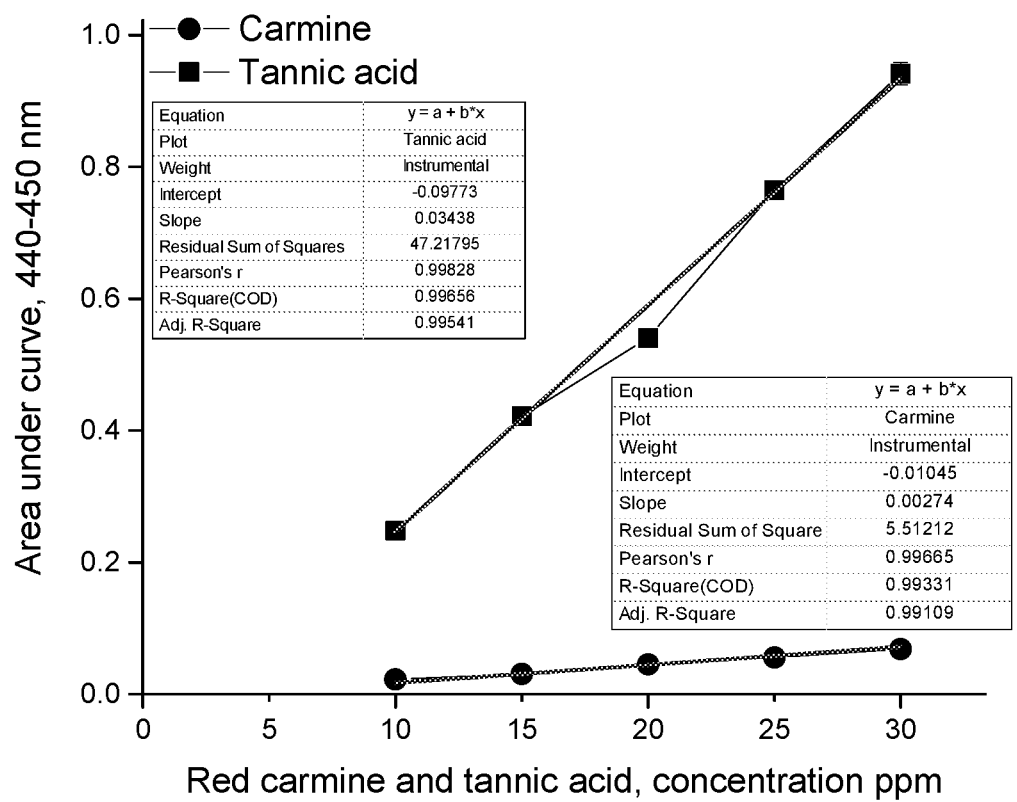
FIG. 3D shows a secons set of Beer's law standard concentration curves for red carmine and tannic acid.
Figure 3E:
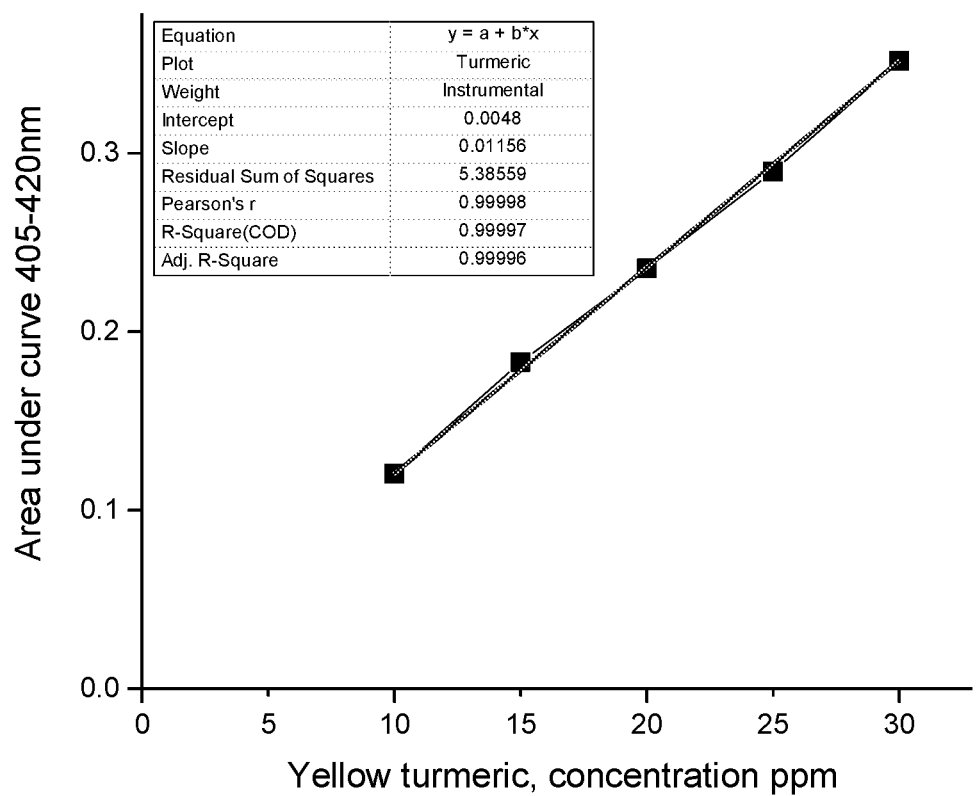
FIG. 3E shows a Beer's law standard concentration curve for yellow turmeric.
Figure 3F:
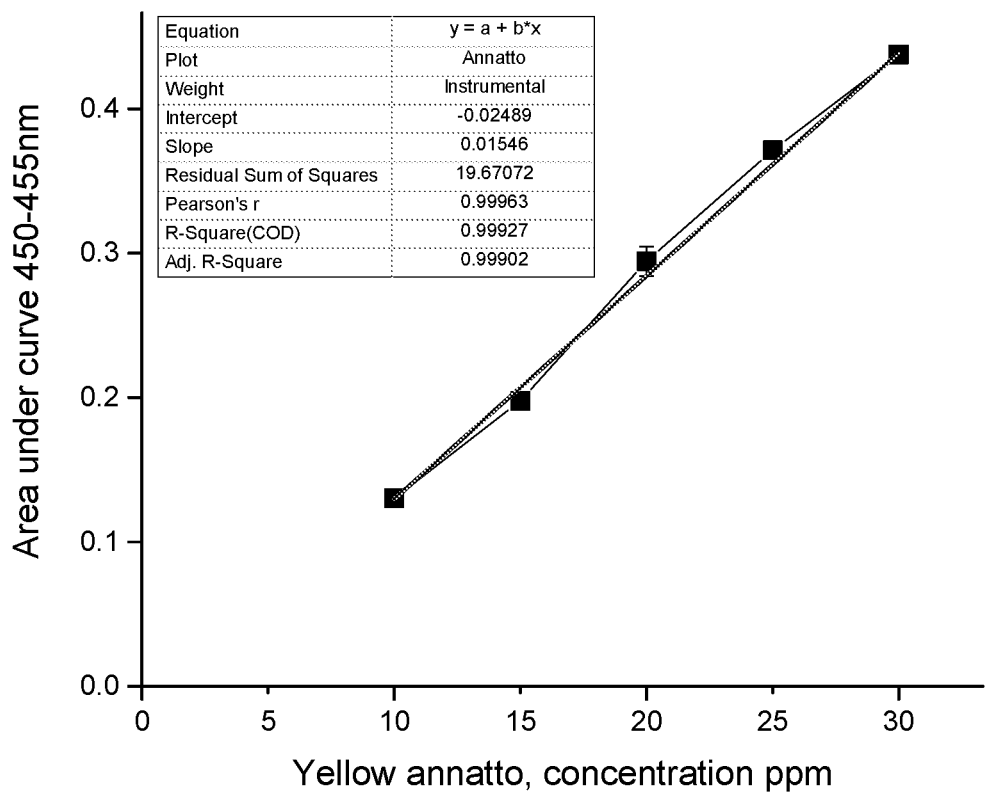
FIG. 3F shows a Beer's law standard concentration curve for yellow annatto.
Figure 3G:
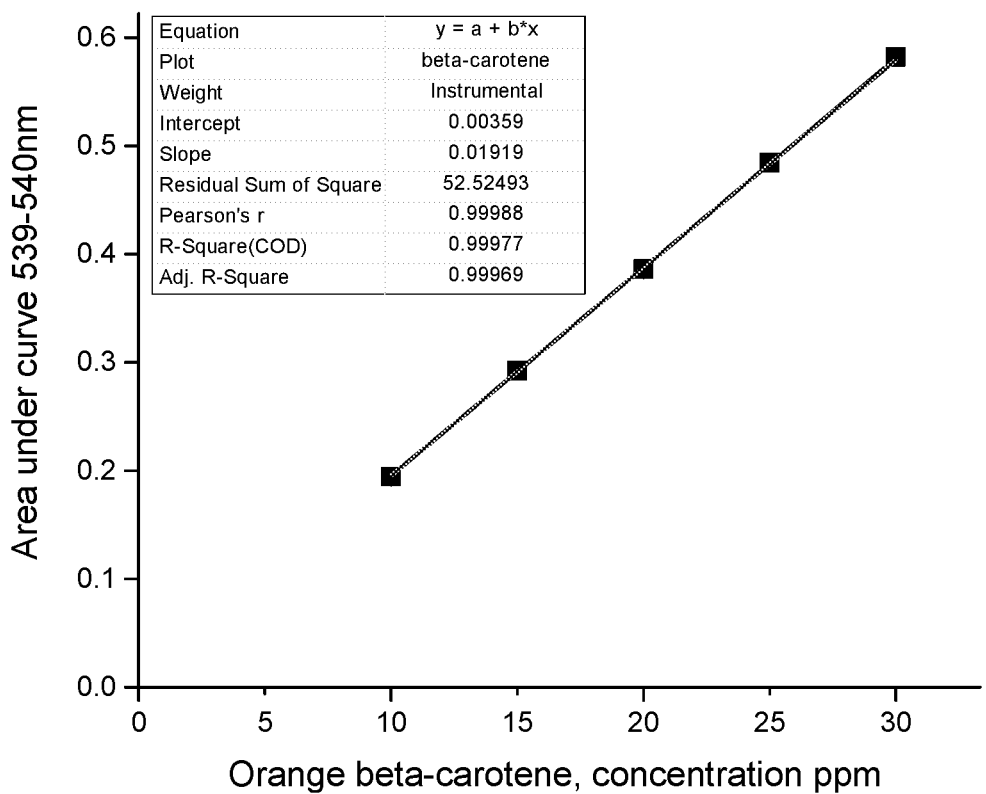
FIG. 3G shows a Beer's law standard concentration curve for orange beta-carotene.
Figure 3H:
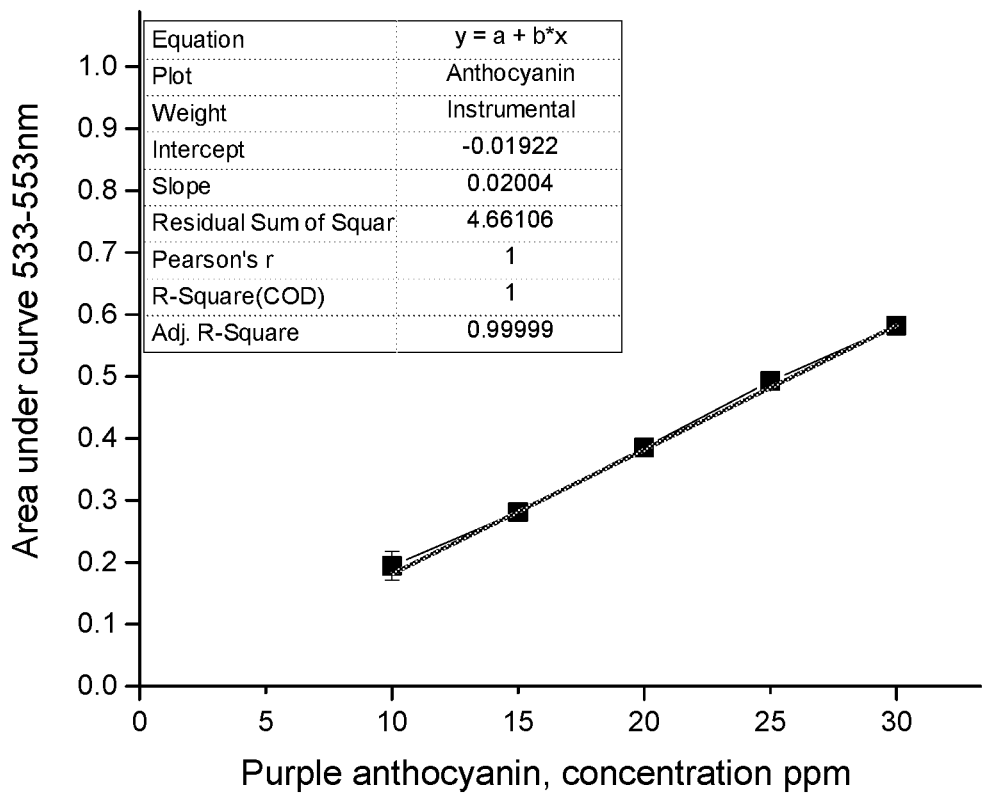
FIG. 3H shows a Beer's law standard concentration curve for purple anthocyanin.

To estimate the dye concentration (ppm), the "area under the curve" of each absorption spectrum was used. Area under curve method involves the calculation of integrated value of absorbance with respect to the wavelength between two selected wavelengths such as $\lambda 1$ and $\lambda 2$. For carmine dye treated with tannic acid, the absorption of tannic acid also taken into account because tannic acid also has strong light absorption. By measuring the area under curve for carmine sample treated with tannic acid at 2 different wave length range 510-530 nm and 440-450 nm and using two equations two unknowns, simultaneously concentration of carmine and lactic was calculated. The absorption spectra of dye solutions were recorded in the spectral range 400-700 nm using a Thermo Scientific™ GENESYS 10S UV-Vis spectrophotometer with disposable plastic cuvettes (Methacrylate). The area under curve between $\lambda 1$ and $\lambda 2$ were calculated by Spectragryph v1.2.9 software. The readings were taken between 450-455 nm for annatto (yellow color), between 405-420 nm for turmeric (yellow color), between 510-530 nm for carmine (red color), between 633-634 nm for chlorophyll (green color), between 610-620 nm for spirulina (blue color), between 539-540 nm for beta-carotene (orange color), between 533-553 nm for anthocyanin (purple color), and between 440-450 nm for tannic acid. The area under curve for each dye is shown in FIGS. 3A (green chlorophyll), 3B (blue spirulina), 3C (red carmine and tannic acid 510-530 nm), 3D (red carmine and tannic acid 440-450 nm), 3E (yellow turmeric), 3F (yellow annatto), 3G (orange beta-carotene), and 3H (purple anthocyanin).

Desorption or dissolution (bleeding) of dye from the colored lactic bacteria, baker's yeast, and microparticulated whey protein was measured by spectrophotometry and comparison to the standard concentration curves shown in FIGS. 3A-3H. The results for the microparticulated whey protein are reported in Table 1 below.

The acceptable set-limit (by industry) of lake bleeding based on the test procedure is below 10 ppm. The dye bleeding of stained baker's yeast and lactic bacteria cells were below 10 ppm, in the acceptable set-limit (by industry).

Colored microparticulated whey proteins (SIMPLESSE®) exhibit high dye bleeding, well above the acceptable range. Proteins have pH dependence solubility, they show the maximum insolubility at their pI (isoelectric point) around 4.5 (Pelegrine, D. H. G. and C. A. Gasparetto, Whey proteins solubility as function of temperature and pH. *LWT—Food Science and Technology*, 2005. 38(1): p. 77-80). At this pH, since the protein has the least solubility, it can retain the dye molecules and act as an effective dye vehicle. Microparticulated proteins may also be a suitable substitute for traditional lake compounds under certain other conditions.

Figure 4:
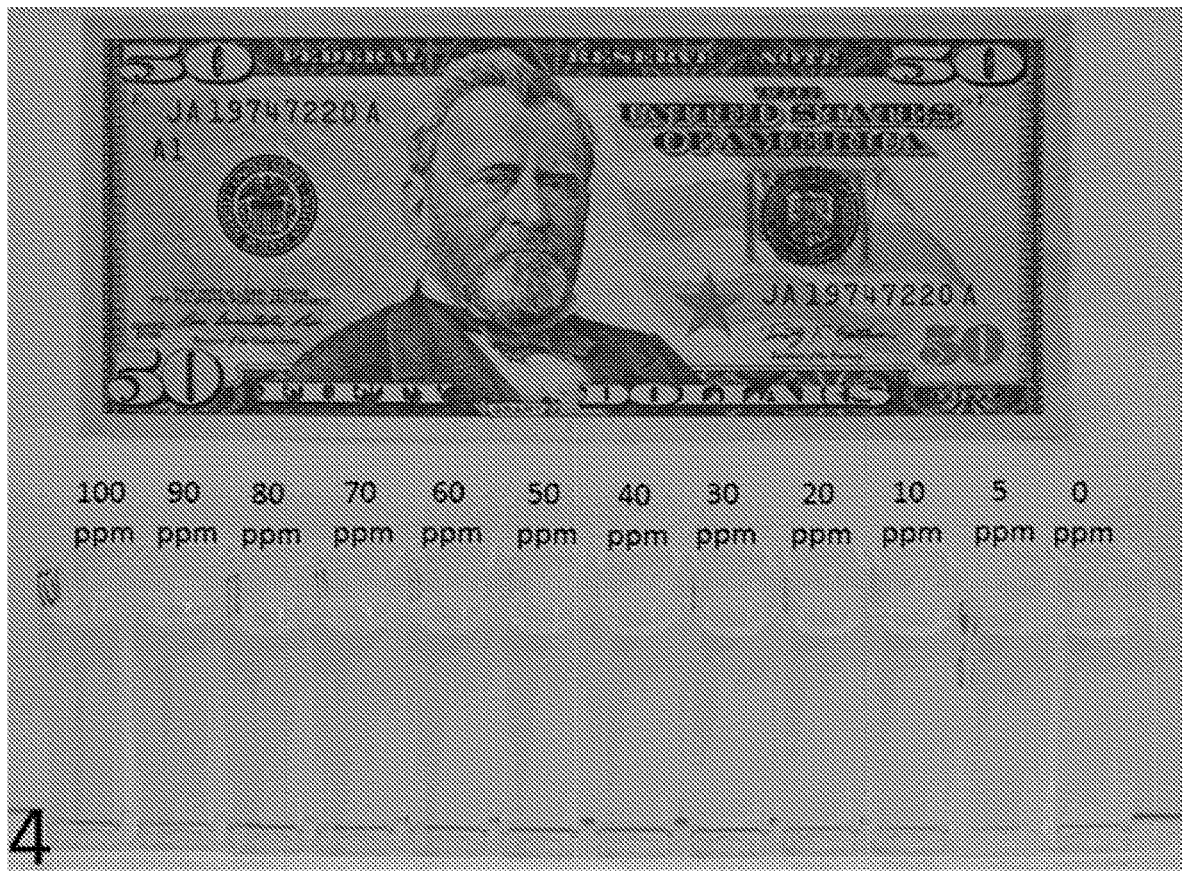
FIG. 4 is a photograph showing solutions of dyes with concentrations of zero, 5, 10, 20, 30, 40, 50, 60, 70, 80, 90 and 100 ppm of spirulina dye, blue.
Figure 5:
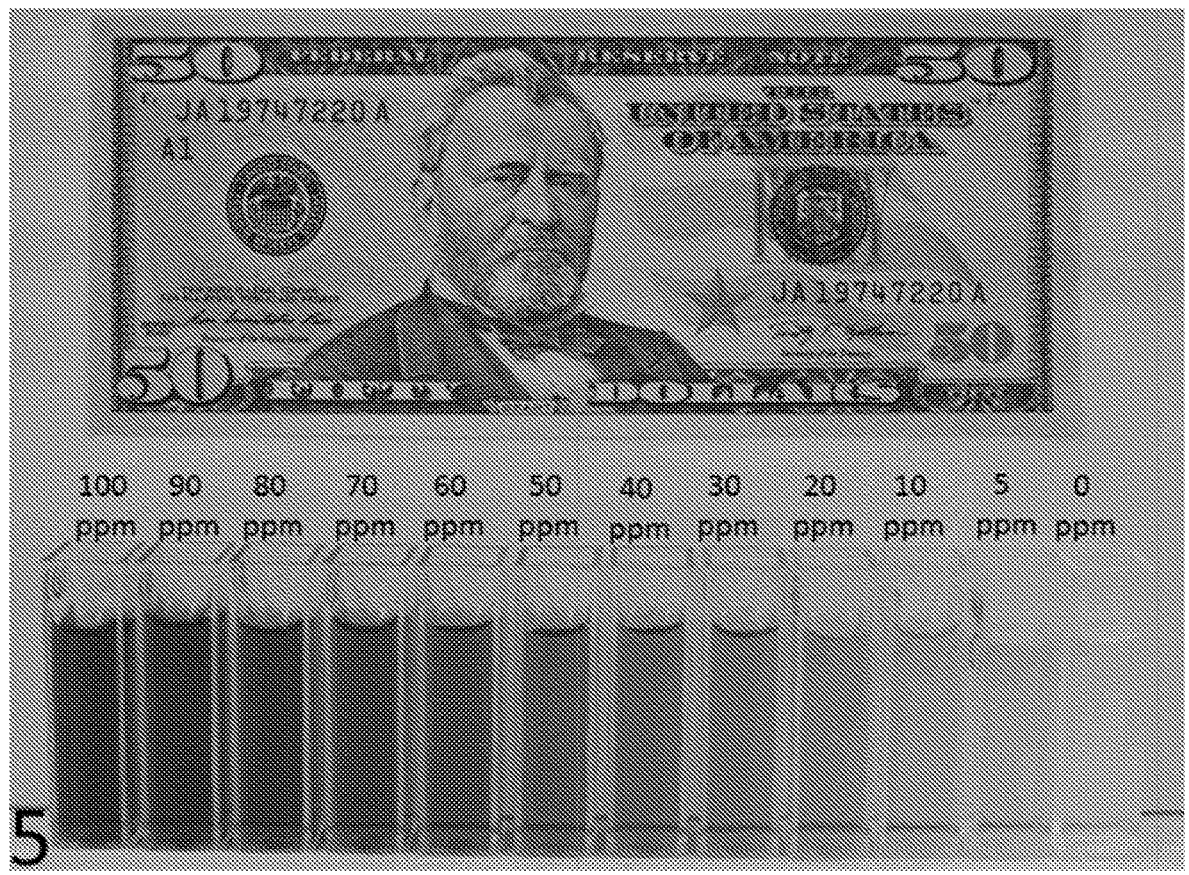
FIG. 5 is a photograph showing solutions of dyes with concentrations of zero, 5, 10, 20, 30, 40, 50, 60, 70, 80, 90 and 100 ppm of chlorophyll dye, green.
Figure 6:
FIG. 6 is a photograph showing solutions of dyes with concentrations of zero, 5, 10, 20, 30, 40, 50, 60, 70, 80, 90 and 100 ppm of carmine dye, red.
Figure 7:
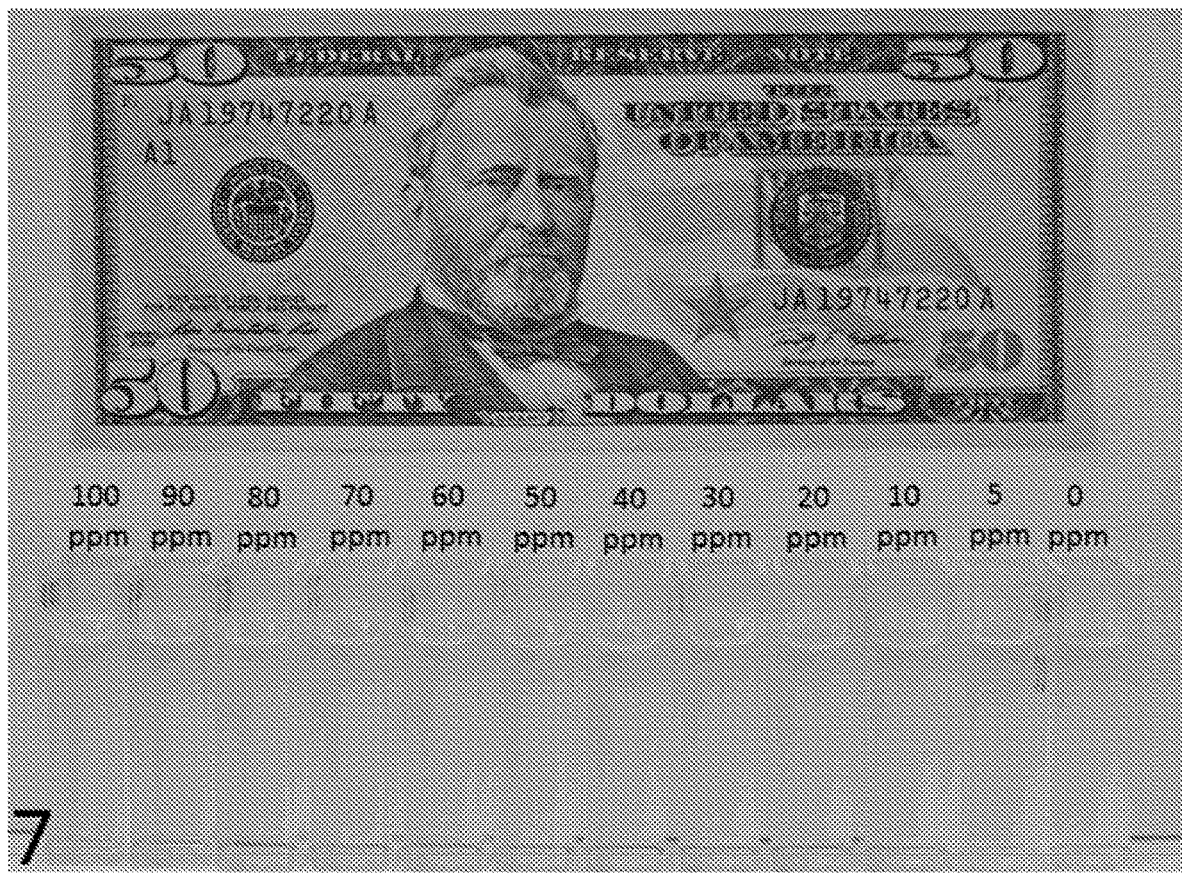
FIG. 7 is a photograph showing solutions of dyes with concentrations of zero, 5, 10, 20, 30, 40, 50, 60, 70, 80, 90 and 100 ppm of turmeric dye, yellow.

To aid the visual guide for quantitative amount of dye dissolved into the water as the result of bleeding, the color intensity of dye solutions in concentration range of zero to 100 ppm (part per million) are shown in FIG. 4 for blue (spirulina), FIG. 5 for green (chlorophyll), FIG. 6 for red (carmine) and FIG. 7 for yellow (turmeric). Solution of blue (spirulina) and yellow (turmeric) have relatively lower color intensity compared with green (chlorophyll) and red (carmine).

In sum, this example demonstrates that protein-containing substrates, such as biologically inactivated single-celled organisms or microparticulated proteins, can be used as a substitute for alumina-based lakes in certain applications.

Those skilled in the art will recognize, or be able to ascertain using no more than routine experimentation, numerous equivalents to the specific materials and methods described herein. Such equivalents are considered to be within the scope of this disclosure and encompassed by the following claims.

We claim:

1. A colorant particle comprising:
   (a) an insoluble substrate comprising one or more proteins; and
   (b) a dye that is adsorbed onto the insoluble substrate;
   wherein the colorant particle is both insoluble in a liquid system and dispersible within a liquid system or onto a solid surface
   wherein the insoluble substrate is part of or all of a biologically inactivated single-celled microorganism denatured to be insoluble and inactivated, and selected from the group consisting of a lactic acid bacterium, a baker's yeast, and a brewer's yeast.

2. The colorant particle of claim 1, wherein the insoluble substrate is less than 10%, less than 5%, or less than 1%

TABLE 1

Desorption/dissolution of dye from microparticulated whey protein (SIMPLESSE ®)

Dye Bleeding (ppm) from Microparticulated Whey Protein (Simplesses ®)

| Color | pH 3.5 | pH 4.5 | pH 5.5 | pH 6.5 | pH tap water (6.9-7.1) |
|---|---|---|---|---|---|
| Yellow turmeric | 7.7 ppm | 2.1 ppm | 65.3 ppm | 47 ppm | 96.2 ppm |
| Green chlorophyll | 0.5 ppm | 0.3 ppm | 50 ppm | 55.2 ppm | 36.7 ppm |
| Red carmine | 0.9 ppm | 1.5 ppm | 17.6 ppm | 46.7 ppm | 52.2 ppm |
| Blue spirulina | 14.4 ppm | 7.5 ppm | 65.3 ppm | 19 ppm | 18.2 ppm | insoluble metal salts by weight; or wherein the insoluble substrate is less than 10%, less than 5%, or less than 1% alumina by weight.

3. The colorant particle of claim 1, wherein the insoluble substrate comprises a microparticulated protein or textured plant protein.

4. The colorant particle of claim 1, wherein the colorant particle is highly dispersible within the liquid system or onto the solid surface, such that when dispersed, the dispersion density of the colorant particles within any two portions of the liquid system or the solid surface does not vary by more than 20%.

5. A composition comprising two or more colorant particles of claim 1, wherein the colorant particles are dispersed within a liquid system, within a solid, or onto a solid surface.

6. The composition of claim 5, wherein the colorant particles are highly dispersed within the liquid system, within the solid, or onto the solid surface, such that the dispersion density of the colorant particles within any two portions of the liquid system, solid, or solid surface does not vary by more than 20%.

7. The composition of claim 5, wherein the composition has a different color than the composition would have in the absence of the two or more colorant particles.

8. A consumer product comprising the colorant particle of claim 1.

9. The consumer product of claim 8, comprising two or more of the colorant particles dispersed within a liquid system, within a solid, or onto a solid surface.

10. A method for coloring a consumer product, comprising contacting a precursor system that ultimately forms part or all of the consumer product with two or more colorant particles claim 1, whereby the two or more colorant particles become dispersed within or on the precursor system.

11. The method of claim 10, wherein the precursor system is a liquid system or a solid surface.

12. The method of claim 11, whereby the colorant particles become highly dispersed within the liquid precursor system or onto the solid surface, such that the dispersion density of the colorant particles within any two portions of the liquid precursor system or solid surface does not vary by more than 20%.

13. A method of making a colorant particle comprising adsorbing a dye onto an insoluble substrate comprising one or more proteins, whereby a colorant particle that is both insoluble in a liquid system and dispersible within the liquid system or onto a solid surface is produced wherein the insoluble substrate is part of or all of a biologically inactivated single-celled microorganism denatured to be insoluble and inactivated, and selected from the group consisting of a lactic acid bacterium, a baker's yeast, and a brewer's yeast.

14. The method of claim 13, wherein the insoluble substrate comprises a microparticulated or textured protein.

15. A method of making a colorant particle from a biologically inactivated single-celled microorganism or a microparticulated protein particle, the method comprising the steps of:

(a) adding a dye to and acidifying an aqueous solution that is in contact with a biologically inactivated single-celled microorganisms or microparticulated protein particle; and (b) subsequently raising the pH of the aqueous solution that is in contact with the biologically inactivated single-celled microorganism or microparticulated protein particle;

whereby the dye is stably adsorbed to the biologically inactivated single-celled microorganism or microparticulated protein particle to form a colorant particle wherein the biologically inactivated single-celled microorganism or the microparticulated protein particle is denatured to be insoluble and inactivated, and selected from the group consisting of a lactic acid bacterium, a baker's yeast, and a brewer's yeast.

16. The method of claim 15, wherein step (a) of acidifying the aqueous solution comprises lowering the pH of the aqueous solution to below 4.0.

17. The method of claim 15, wherein step (b) of subsequently raising the pH of the aqueous solution comprises raising the pH of the aqueous solution to above 6.0.

* * * * *